(12) United States Patent
Maa et al.

(10) Patent No.: US 10,609,798 B1
(45) Date of Patent: Mar. 31, 2020

(54) CIRCADIAN LIGHTING APPARATUS

(71) Applicant: Aleddra Inc., Renton, WA (US)

(72) Inventors: Chia-Yiu Maa, Bellevue, WA (US); Chun-Te Yu, Bellevue, WA (US)

(73) Assignee: ALEDDRA INC., Renton, WA (US)

( * ) Notice: Subject to any disclaimer, the term of this patent is extended or adjusted under 35 U.S.C. 154(b) by 0 days.

(21) Appl. No.: 16/235,058

(22) Filed: Dec. 28, 2018

(51) Int. Cl.
*H05B 45/20* (2020.01)
*H05K 1/02* (2006.01)
*H03K 19/20* (2006.01)
*H01L 33/50* (2010.01)

(52) U.S. Cl.
CPC .......... *H05B 45/20* (2020.01); *H01L 33/502* (2013.01); *H03K 19/20* (2013.01); *H05K 1/0274* (2013.01)

(58) Field of Classification Search
None
See application file for complete search history.

(56) References Cited

U.S. PATENT DOCUMENTS

| | | | | |
|---|---|---|---|---|
| 2008/0091250 A1* | 4/2008 | Powell | ............... | A61M 21/00 607/90 |
| 2014/0296060 A1* | 10/2014 | Chen | ............... | B01J 23/50 502/159 |
| 2015/0022093 A1* | 1/2015 | Smith | ............... | A61N 5/0618 315/151 |
| 2015/0151015 A1* | 6/2015 | Bugenske | ............... | B29D 11/00 422/24 |
| 2018/0043130 A1* | 2/2018 | Moore-Ede | ............... | G16H 20/30 |
| 2019/0168204 A1* | 6/2019 | Van Buskirk | ............... | B01J 35/004 |

* cited by examiner

*Primary Examiner* — Dedei K Hammond
(74) *Attorney, Agent, or Firm* — Han IP PLLC; Andy M. Han

(57) ABSTRACT

A circadian lighting apparatus includes a housing, two light sources, and a control logic. The first light source is a blue-enriched light source for stimulating human to a high circadian mode. The second light source is a blue-depleted light source for calming down human to a low circadian mode. The criteria of a good circadian lighting apparatus are identified. When coated with an anti-bacterial photocatalytic coating on the exterior, the circadian lighting apparatus becomes a disinfecting equipment that can kill the airborne bacteria and viruses that make contact to its anti-bacterial photocatalytic coated surface.

8 Claims, 4 Drawing Sheets

CIRCADIAN LIGHTING APPARATUS

BACKGROUND

Technical Field

The present disclosure pertains to the field of lighting devices and, more specifically, proposes a circadian lighting apparatus.

Description of Related Art

It is well known that circadian rhythm affects the behavior of animals, including human. Studies have also shown circadian lighting which is a lighting device based on a circadian rhythm could improve the recovery of patients in hospital. A circadian lighting works this way: a blue-enriched light stimulates the awareness and the alert level of the human body, thus suitable for working hours; a blue-depleted light clams down the human body to a lower alert level, thus suitable for off-work hours. Moreover, it is identified that human's circadian response curve over light spectrum differs than human's visual response curve. FIG. 1 shows the spectral power distribution (SPD) of six different light sources (source: International Well Building Institute, https://standard.wellcertified.com/sites/default/files/Melanopic%20Ratio.xlsx.). The bell-shape curve on the left of each figure is the circadian response curve, or the melanopic curve. The bell-shape curve on the right of each figure is the visual response curve, or the photopic curve. It can be seen from the figures that sunlight has the most evenly distributed SPD. The SPD of man-made light sources differs from one to the other. Some light source (e.g., 4000K LED) has a significant higher SPD in the blue light range 450-490 nm. The SPD of man-made light sources also differs greatly in the visible light range (the area covered under the visual response curve).

Given different light sources have different SPDs, then how to select a light source for high circadian lighting and how to select a light source for low circadian lighting? One commonly used measurement in identifying the circadian quality of a light source is the melanopic vs. photopic ratio, also known as the M/P ratio. It compares the weighted SPD under the melanopic curve to the weighted SPD under the photopic curve. The M/P ratio of the six light sources in FIG. 1 are shown in FIG. 2. A light source with a higher M/P ratio is considered to be more suitable for a high circadian lighting application. From FIG. 2 the sunlight has the highest M/P ratio 1.128, which may lead to the conclusion that the M/P ratio is a good measure on the circadian quality of a light source. However, it is argued that the M/P ratio alone is not adequate in determining the circadian quality of a lighting device for two reasons. Firstly, a light source with a high M/P ratio may not be a good light (in the sense of general lighting) to begin with. Consider a blue light with almost 95% of its SPD in the blue wavelength range, therefore it has an extremely high M/P ratio (much higher than that of sunlight). Yet, a blue light isn't a good choice for general circadian lighting because of its limited range of SPD. This leads to an observation that a suitable lighting device for a high circadian mode needs not only have a significant SPD under the melanopic curve but also has a good overall lighting quality. Judging the circadian quality of a lighting device solely on its M/P ratio is insufficient. A measurement on overall lighting quality should be part of the qualification of a good circadian light source. One generally accepted light quality measurement is the color rendering index (CRI).

The second limitation of the M/P ratio is that there is no consideration of the SPD in the UV wavelength (<400 nm). A lighting device having a strong SPD in the UV range, regardless its M/P ratio, is not suitable for general circadian lighting use because of the risk of UV light on causing skin cancer. It is suggested to also include a qualification on the UV spectral power when evaluating a good general circadian lighting device.

It is proposed that a well-designed circadian lighting apparatus should meet these five essential qualifications simultaneously. Firstly, it should provide a good quality light with a high CRI regardless its lighting modes or color temperature. Secondly, it should be UV-free or with a negligible UV SPD. Thirdly, a good circadian lighting apparatus should support at least two lighting modes: a high circadian lighting mode (for high biological awareness) and a low circadian lighting mode (for calming down biological awareness). A high circadian lighting mode requires the use of a blue-enriched light source and a low circadian lighting mode necessitates the use of a blue-depleted light source. Fourthly, it should support a gradual transition from a high circadian lighting mode to a low circadian lighting mode and vice versa. An abrupt switching from a blue-enriched light to a blue-depleted light is unnatural and uncomfortable. It is more comfortable to human eyes if the light changes from a blue-enriched mode to a blue-depleted mode gradually and continuously. Lastly, a circadian lighting apparatus provides a means for adjusting its light according to a circadian schedule automatically.

In addition to the five essential qualifications, there are two additional requirements that would greatly enhance the user experience. Firstly, the control logic can dim the first and the second light sources. Dimming gives the control to the user according to his practical needs. Secondly, the circadian lighting apparatus should also provide manual override option for overriding the preconfigured circadian schedule such that a user can set the light apparatus to either the high circadian lighting mode (for better awareness even at night if needed) or the low circadian lighting mode (for calming down the body alertness even during the day time) according to his needs.

SUMMARY

The present disclosure introduces a circadian lighting apparatus meeting all six requirements listed above, and its extension with anti-bacterial coating for anti-bacterial lighting application.

In one aspect, the circadian lighting apparatus comprises a housing, two light sources, and a control logic. To meeting the requirement of being a good quality light suitable for general lighting application, both light sources have CRI>80. Their SPD in sub-400 nm wavelength range is less than <3%, meeting the negligible UV requirement. The reason that negligible UV SPD is used rather than UV-free are twofold. Firstly, it may be too costly for using a 100% UV-free light source. Secondly, a light source with a small UV SPD is generally acceptable. The fluorescent light sources shown in FIG. 1 are good examples with small UV SPD and they are very acceptable for general lighting use.

The first light source is blue-enriched with SPD>20% in the 410-490 nm wavelength range. The second light source is blue-depleted with SPD<5% in the 410-490 nm wavelength range. The percentage of SPD in the 410-490 nm is used, rather than the M/P ration, for it directly measure the SPD of the blue light of a light source. The FIG. 1 highlights the 410-490 nm wavelength range with a rectangle box on the SPD graphs, and the FIG. 2 shows the percentage SPD in 410-490 nm vs. the overall SPD for all six sample light sources.

For the present disclosure, the maximum wattage of the first light source equals to the maximum wattage of the second light source. Given a fixed overall wattage consumption W, the control logic of the present disclosure may tune continuously the color of the apparatus according to the following formula:

$$W = Y \times W1 + (1-Y) \times W2$$

Where Y in [0%, 100%] represents the power consumption percentage of the first light source, (1−Y) represents the power consumption percentage of the second light source, and W1 and W2 represent the maximum wattage of the first and the second light sources, respectively. Moreover, the control logic of the present disclosure may tune automatically the color temperature of the apparatus according to a circadian schedule. Without a circadian schedule and the means of enforcing it automatically, a color-tunable light apparatus is merely color-tunable, but can't be regarded as a circadian lighting device for the lack of a circadian schedule. The circadian schedule may be stored in the present disclosure or it may be acquired via a communication network.

In some embodiments, the maximum wattage of the first light source equals to the maximum wattage of the second light source. So the color-tuning formula becomes:

$$W = Y \times W \pm (1-Y) \times W$$

Where W represents the maximum wattage of the first and the second light sources. With this formula, if the color temperature of the first light source is C1 and the color temperature of the second light source is C2, then the above power consumption formula could effectively render any color temperature between C1 and C2 by setting a proper percentage Y.

The color-tuning formula implies that control logic can dim both light sources according to a linear combination of the first and the second light sources. There are occasions where a user may want to dim the complete apparatus. The color-tuning formula with dimming would become:

$$W = (Y \times W1 + (1-Y) \times W2) \times D$$

Where D is the dimming level in [0%, 100%]. Thus, in some embodiments, the control logic may dim the first and the second light sources simultaneously.

In some embodiments, the control logic of the present disclosure provides a means to override the circadian schedule for accommodating the lighting needs outside the normal circadian schedule according to user's needs.

It is easy to find a good blue-enriched light source at a reasonably low cost. This however is not the case for blue-depleted light source. It may be more cost-effective to combine a regular light source with a blue-light filtering medium for forming an effective blue-depleted light source. Therefore, in some embodiments, the second light source comprises a third light source and a blue-light filtering medium. The light of the third light source itself may not have its SPD<5% in the 410-490 nm wavelength range. After passing through the blue-light filtering medium, the filtered light of the third light source has a CRI>80, a SPD<5% in 410-490 nm wavelength range and <3% in the sub-400 nm wavelength range. It is also possible to use UV filter with a native light source in meeting the UV-free requirement.

In some embodiments, each of the two light sources may be a plurality of light emitting diodes (LED's). The FIG. 3 shows the SPD of LED light source with CRI>80 at these color temperatures: 5000K, 4000K, 2700K, and 2700K with blue-light filtered. The 5000K LED has a SPD percentage 26.5% in 410-490 nm range and <3% in UV (sub-400 nm) range, and thus is a good option for the first light source of the present disclosure. The 2700K LED with CRI>80, though meeting the near UV-free requirement (SPD percentage <3% in sub-400 nm range), its SPD percentage in the 410-490 nm range is 10.5%, exceeding the 5% SPD threshold. After filtering the light 2700K LED with a blue-light filter, the filtered light now has a reduced SPD percentage at 3.9% in the 410-490 nm range, which qualifies for the second light source of the present disclosure.

In some other embodiments, each of the two light sources may be a plurality of organic LEDs (OLED's). It is foreseeable in using a different lighting technology for each of the two light sources of the present disclosure. For example, using LED for the first light source and OLED for the second light source. In this case, the power consumption of the two light sources may be different because they have different efficacy (lm/w) and thus would need to consume different wattage for generating the same level of light output.

The continuous color-tuning of the apparatus mentioned above may require a rather complicate design of the control logic. In some cases, a simplified control logic that approximate the continuously color-tuning of the apparatus may suffice. Therefore, in some embodiments, the continuous color-tuning of the apparatus according to a circadian schedule may be approximated by a discrete color-tuning with a fixed number of linear combinations of the first and the second light sources.

In some embodiments, the exterior of the housing of the present disclosure is at least partially coated with an anti-bacterial photocatalytic film. With the coating, the circadian lighting apparatus now becomes a disinfection equipment. When the anti-bacterial photocatalytic film is activated, it could kill the airborne bacteria and viruses making contact with it.

In another aspect, the circadian lighting apparatus comprises a housing, at least two light sources, and a control logic. At least one light source has a SPD>20% in the 410-490 nm wavelength range, and at least one has a SPD<5% in the 410-490 nm wavelength range. The control logic is capable of switching the light output of the apparatus from one light source to another light source according to a circadian schedule. Moreover, the exterior of the circadian lighting apparatus is at least partially coated with an anti-bacterial photocatalytic film.

In some embodiments, the anti-bacterial photocatalytic film is photocatalytic activated by the light of the circadian lighting apparatus. In some other embodiments, the anti-bacterial photocatalytic film is photocatalytic activated by ambient light with at least 95% of a spectral power distribution (SPD) in a visible light wavelength range greater than 400 nm. Most of the light sources for general lighting, such as incandescent bulbs, fluorescent bulbs, LED bulbs, generate at least 95% of a spectral power distribution (SPD) in a visible light wavelength range greater than 400 nm, and so is the sunlight. When the circadian lighting apparatus is turned on, the light coming out of the apparatus can activate the anti-photocatalytic film. But even when the circadian lighting apparatus is turned off, the ambient light, such as sunlight or other indoor light source, may still activate the anti-photocatalytic film, thus continually providing the anti-bacterial/anti-viral protection to the environment the apparatus is installed.

In some embodiments, a main active ingredient of the anti-bacterial photocatalytic film is titanium dioxide ($TiO_2$). In some other embodiments the main active ingredient is rhombus-shape anatase-type titanium dioxide ($TiO_2$). As shown in U.S. Pat. No. 9,522,384 by Liu L. et al, the rhombus-shape anatase-type titanium dioxide has a much higher volume density than the sphere-shape anatase-type titanium dioxide, thus it is more effective in the photocatalytic killing of bacteria and viruses.

In some embodiments, the anti-bacterial photocatalytic film may contain at least one other active metal ingredient such as but not limited to, silver, gold, copper, zinc, or nickel. These metals when embedded in the photocatalyst are known to enhance the photocatalytic activity with visible light. Some photocatalytic film may contain more than one type of metals for a better photocatalytic effectiveness.

The titanium dioxide is classified as a semiconducting photocatalyst. Recently technology breakthrough has demonstrated that noble metal nanoparticles such as gold (Au) and silver (Ag) can are a class of efficient photocatalysts working by mechanisms distinct from those of semiconducting photocatalysts (https://pubs.rsc.org/en/content/article-landing/2013/gc/c3gc40450a#!divAbstract). The present disclosure is not limited to the use of semiconducting photocatalysts. In some embodiments, the main active ingredient of the anti-bacterial photocatalytic film is a noble metal nanoparticle comprising gold (Au) or sliver (Ag).

BRIEF DESCRIPTION OF THE DRAWINGS

The accompanying drawings are included to aid further understanding of the present disclosure, and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of lighting apparatuses having different form factors.

EXAMPLE IMPLEMENTATIONS

Figures 1, 2:
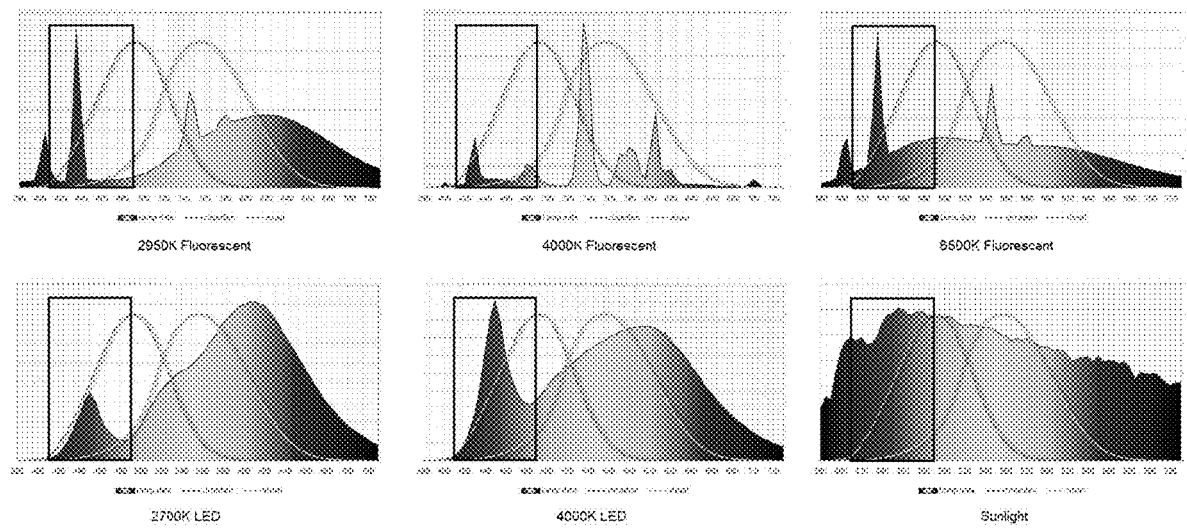
FIG. 1 shows the spectral power distribution of six commonly seen light sources.
FIG. 2 lists the M/P ratio and the percentage SPD in the 410-490 nm range.
Figure 3:
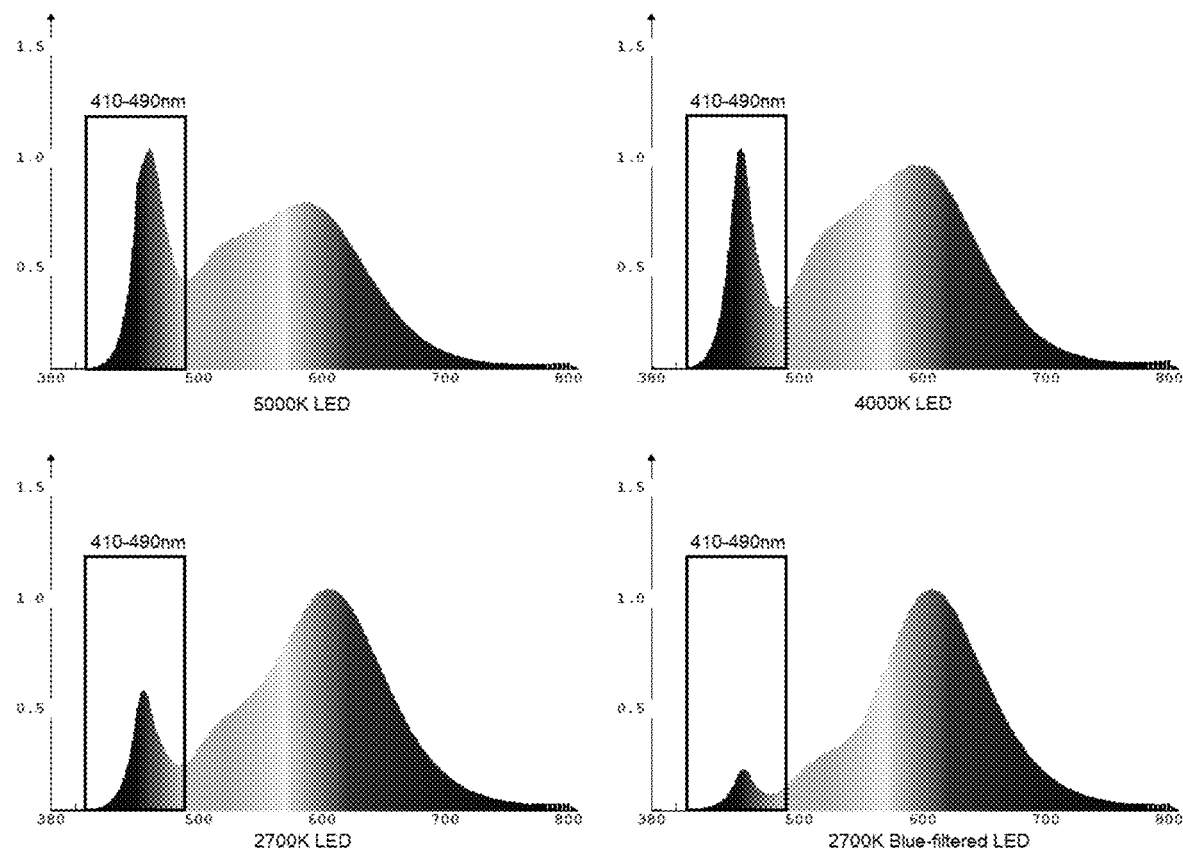
FIG. 3 compares the SPD of four different LED light sources.
Figure 4:
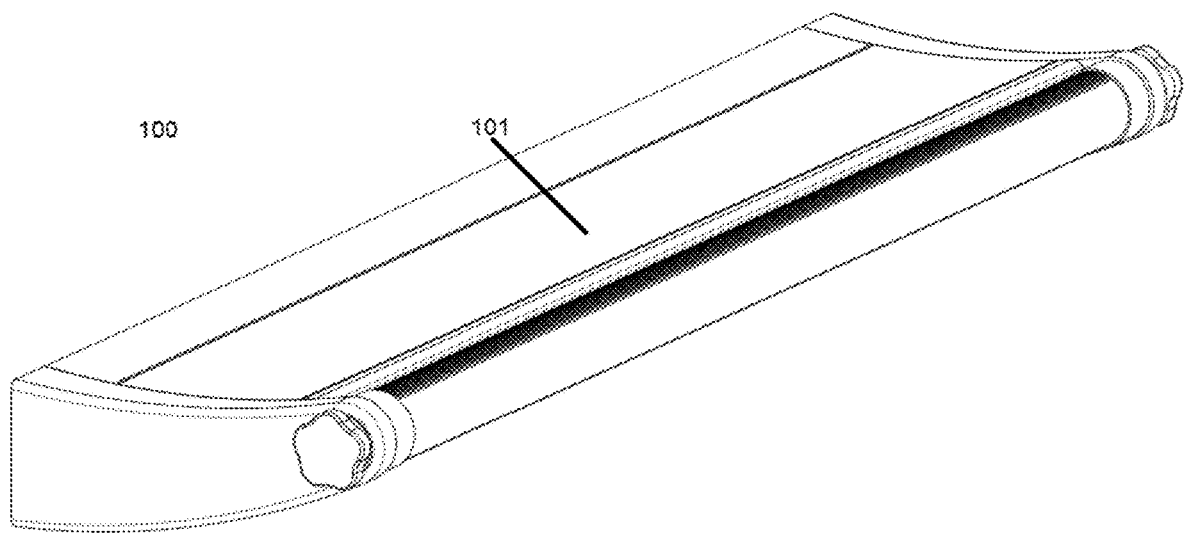
FIG. 4 schematically depicts the exterior diagram of a circadian lighting apparatus.

The FIG. 4 is an elongated lighting apparatus 100 of the present disclosure in the form of an overbed lighting fixture. This apparatus has an up light 101 and a down light (not shown). The entire exterior of the fixture 1000 is coated (though not shown) with a film of the rhombus-shape anatase-type $TiO_2$. When the lighting fixture is turned on, the $TiO_2$ film can be activated by the light of the lighting fixture. When the lighting fixture is off, the $TiO_2$ film may still be activated by the ambient light such as sunlight or the light from other fixtures.

Figure 5:
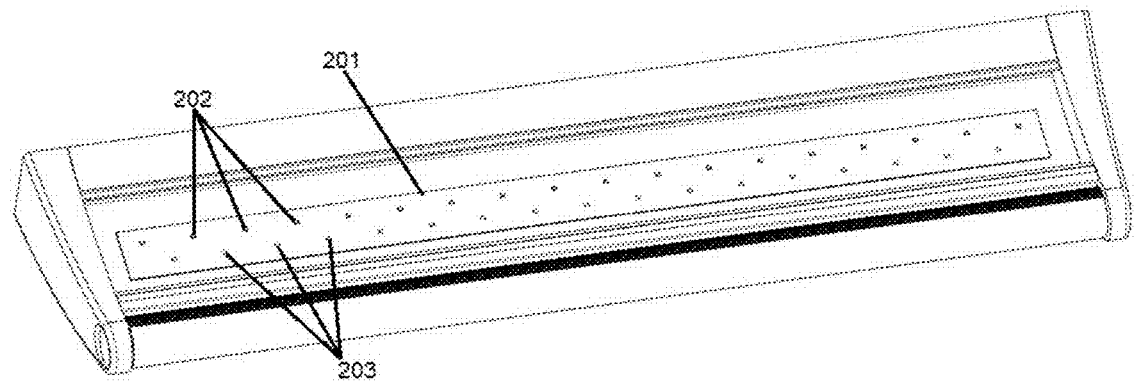
FIG. 5 schematically depicts an interior diagram of a circadian lighting apparatus using blue-enriched LEDs and blue-depleted LEDs.
Figure 5:
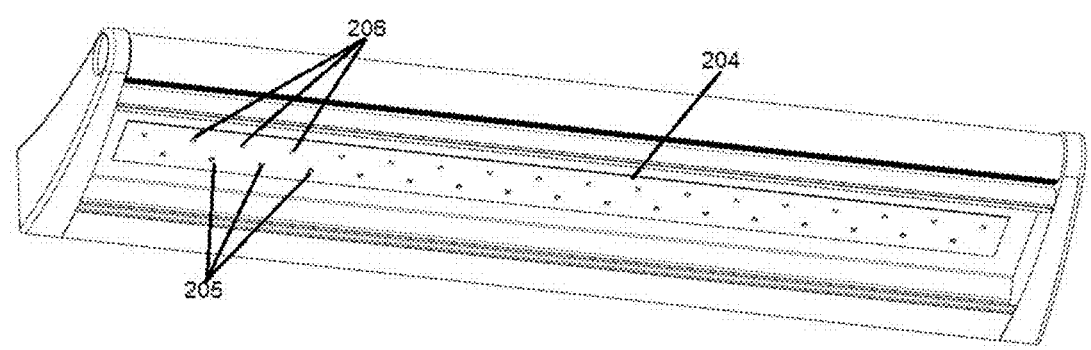

The FIG. 5 shows the PCB boards of the up light and the down light. On the up light PCB board 201, there are two rows of LEDs, the blue-enriched LEDs 202 and the blue depleted LEDs 203. Similarly, on the down light PCB board 204, there are two rows of LEDS, the blue-enriched LEDs 205 and the blue depleted LED 206. All blue-enriched LEDs 202, 205 are 5000K, with CRI>80, and a SPD>20% in 410-490 nm range and <3 in sub-400 nm range. All blue-depleted LEDs 303, 306 are 2700K, with CRI>80, and a SPD<5% in 410-490 nm range and <3 in sub-400 nm range. Both the up light and the down light has the same maximum output wattage.

Though the control logic is not shown in the figures, it stores the following color-tuning circadian schedule over 24 hours based on a discrete linear combination of 5000K an 2700K LEDs:

0:00-6:00: 5000K LED at 0% light output, 2700K LED at 100% light output

6:00-7:00: 5000K LED at 30% light output, 2700K LED at 70% light output

7:00-8:00: 5000K LED at 70% light output, 2700K LED at 30% light output

8:00-9:00: 5000K LED at 90% light output, 2700K LED at 10% light output

9:00-15:00: 5000K LED at 100% light output, 2700K LED at 0% light output

15:00-16:00: 5000K LED at 90% light output, 2700K LED at 10% light output

16:00-17:00: 5000K LED at 70% light output, 2700K LED at 30% light output

17:00-18:00: 5000K LED at 30% light output, 2700K LED at 70% light output

16:00-0:00: 5000K LED at 0% light output, 2700K LED at 100% light output

The discrete color-tuning schedule would gradually increase the proportional light output of the blue-enriched light from 6 to 9 am, maintain the highest circadian effect from 9 am to 3 pm, and then gradually increase the proportional light output of the blue-depleted light from 3 to 6 pm, and keep the blue-depleted light mode from 6 pm to 6 am. This schedule can be used for normal working schedule. It is possible to include a time-shift mechanism in the control logic for shifting the above schedule, say, by 8 hours so it can be used for the workers on a second shift. Though not shown in the figures, the control logic provide three lighting modes for user: circadian mode (by default), daylight mode (5000K), warn white mode (2700K), so that a user can override the default circadian lighting mode according to his needs.

Figure 6:
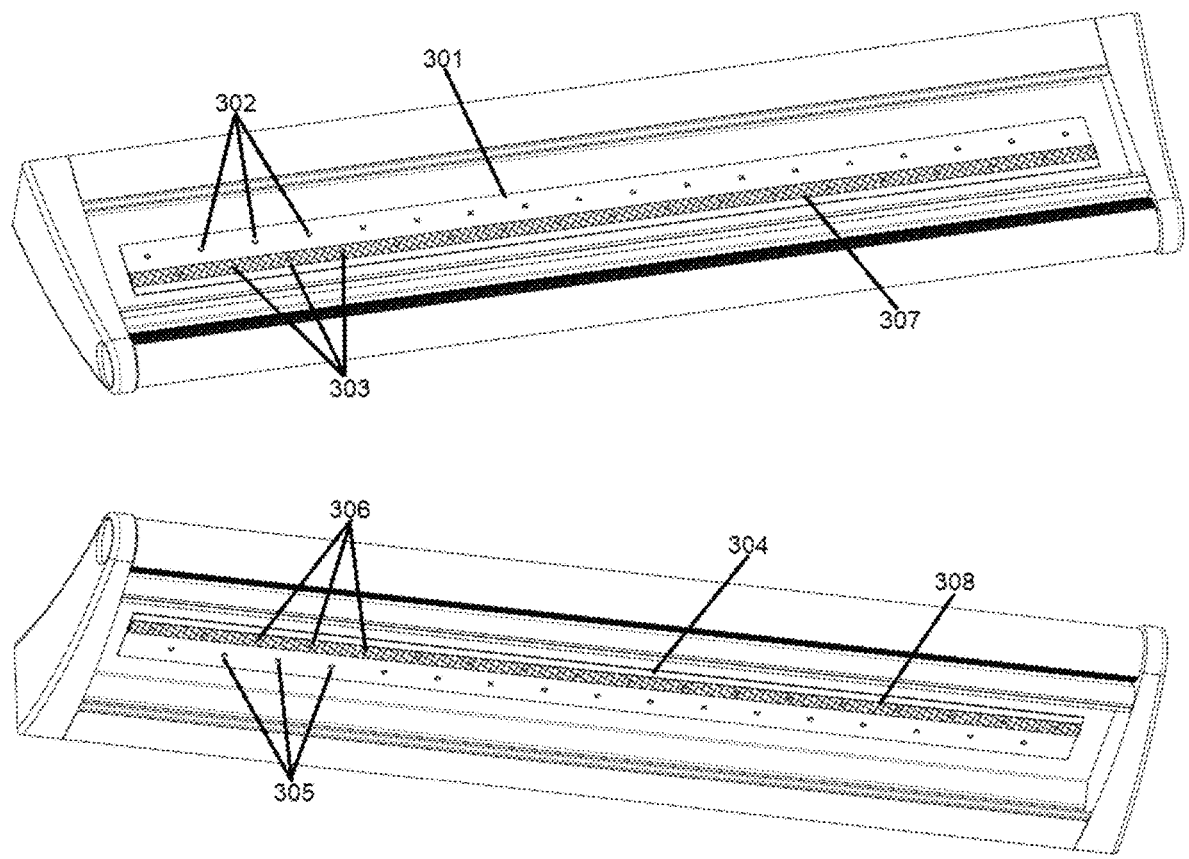
FIG. 6 schematically depicts an interior diagram of a circadian lighting apparatus using blue-enriched LEDs and regular LEDs with a blue-light filter.

The FIG. 6 is another embodiment of the present disclosure. Its exterior and control logic are exactly the same as described above. It has both the up light and the down light. On the up light PCB board 301, there are two rows of LEDs, the blue-enriched LEDs 302 and the 2700K LEDs 303. Similarly, on the down light PCB board, there are two rows of LEDs, the blue-enriched LEDs 305 and the 2700K LED 206. All blue-enriched LEDs 302, 305 are 5000K, with CRI>80 and a SPD>20% in 410-490 nm range and <3 in sub-400 nm range. The 2700K LEDs 303, 306 have CRI>90 and their SPD is >10% in 410-490 nm range. These 2700K LEDs are filtered with the blue-light filters 307, 308, and the filtered light has CRI>80 and a SPD<5% in 410-490 nm range and <3 in sub-400 nm range, thus meeting the requirements for a blue-depleted light source. The CRI of the 2700K LEDs is 90 in order to compensate the reduction of the CRI due to blue-light filtering. If using an 80-CRI 2700K LED, the CRI of the filtered light would drop to 70. By using a 90 CRI LEDs, the filtered light could still meet the required light quality at 80 CRI.

Additional and Alternative Implementation Notes

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A circadian lighting apparatus, comprising:
    a housing;
    two light sources comprising a first light source and a second light source; and
    a control logic,
    wherein:
        the first light source has a color rendering index (CRI) >80, a spectral power distribution (SPD)>20% in a 410-490 nm wavelength range and <3% in a sub-400 nm wavelength range;
        the second light source comprises a third light source and a blue-light filtering medium with a light emitted by the third light source being filtered by the blue-light filtering medium to result in a filtered light that has a CRI>80, a SPD<5% in the 410-490 nm wavelength range and <3% in the sub-400 nm wavelength range;
        the control logic is configured to tune continuously a color temperature of the apparatus by adjusting an output percentage of the first light source and the second light source while maintaining a fixed overall wattage consumption for the apparatus; and
        the control logic is also configured to tune automatically the color temperature of the apparatus according to a circadian schedule.

2. The circadian lighting apparatus of claim 1, wherein a maximum wattage of the first light source equals to a maximum wattage of the second light source.

3. The circadian lighting apparatus of claim 1, wherein the control logic is capable of dimming the first and the second light sources simultaneously.

4. The circadian lighting apparatus of claim 1, wherein the control logic is capable of overriding manually an auto-color-tuning schedule.

5. The circadian lighting apparatus of claim 1, wherein each of the first and second light sources respectively comprises a plurality of light emitting diodes (LEDs).

6. The circadian lighting apparatus of claim 1, wherein each of the first and second light sources respectively comprises a plurality of organic light-emitting diodes (OLEDs).

7. The circadian lighting apparatus of claim 1, wherein a continuous color-tuning of the apparatus according to the circadian schedule is approximated by a discrete color-tuning with a fixed number of linear combinations of an output of the first light source and the second light source at a fixed overall apparatus wattage consumption.

8. The circadian lighting apparatus of claim 1, wherein an exterior of the circadian lighting apparatus is at least partially coated with an anti-bacterial photocatalytic film.

* * * * *